(12) United States Patent
Bishop et al.

(10) Patent No.: US 11,331,221 B2
(45) Date of Patent: May 17, 2022

(54) NEGATIVE PRESSURE WOUND DRESSING

(71) Applicant: ConvaTec Limited, Flintshire (GB)

(72) Inventors: Stephen S. Bishop, Flintshire (GB); Lucy L. Ballamy, Denbighshire (GB); Sarah E. Wroe Nield, Manchester (GB); Duncan Gilding, Flintshire (GB)

(73) Assignee: CONVATEC LIMITED, Flintshire (GB)

( * ) Notice: Subject to any disclaimer, the term of this patent is extended or adjusted under 35 U.S.C. 154(b) by 199 days.

(21) Appl. No.: 16/728,290

(22) Filed: Dec. 27, 2019

(65) Prior Publication Data

US 2021/0196525 A1 Jul. 1, 2021

(51) Int. Cl.
*A61F 13/02* (2006.01)
*A61F 13/00* (2006.01)

(52) U.S. Cl.
CPC .... *A61F 13/0206* (2013.01); *A61F 13/00068* (2013.01); *A61F 13/0213* (2013.01); *A61F 13/0223* (2013.01); *A61F 13/0253* (2013.01); *A61F 2013/00174* (2013.01)

(58) Field of Classification Search
CPC ............ A61F 13/0206; A61F 13/00068; A61F 13/0213; A61F 13/0223; A61F 13/0253; A61F 2013/00174; A61F 13/0203
See application file for complete search history.

(56) References Cited

U.S. PATENT DOCUMENTS

| | | | |
|---|---|---|---|
| 10,016,537 B2 | 7/2018 | Menon et al. | |
| 10,046,096 B2 | 8/2018 | Askem et al. | |
| 10,076,447 B2 | 9/2018 | Barta et al. | |
| 10,076,587 B2 | 9/2018 | Locke et al. | |
| 10,143,784 B2 | 12/2018 | Walton et al. | |
| 10,426,670 B2 | 10/2019 | von Blucher et al. | |
| 10,426,747 B2 | 10/2019 | Johnson | |
| 10,426,874 B2 | 10/2019 | Chien et al. | |
| 10,426,875 B2 | 10/2019 | Blott et al. | |
| 10,426,938 B2 | 10/2019 | Locke et al. | |
| 10,434,015 B2 | 10/2019 | Taylor et al. | |
| 10,434,142 B2 | 10/2019 | Niazi et al. | |
| 10,434,210 B2 | 10/2019 | Olson et al. | |
| 10,434,284 B2 | 10/2019 | Hanson et al. | |
| 10,449,094 B2 | 10/2019 | Donda et al. | |
| D866,756 S | 11/2019 | Allen et al. | |
| 10,463,760 B2 | 11/2019 | Karthikeyan et al. | |

(Continued)

FOREIGN PATENT DOCUMENTS

| EP | 3187204 A1 | 7/2017 |
|---|---|---|
| EP | 3556407 A1 | 10/2019 |

(Continued)

*Primary Examiner* — Susan S Su
*Assistant Examiner* — Eric Rassavong
(74) *Attorney, Agent, or Firm* — Taft Stettinius & Hollister LLP; Ryan O. White; Derek B. Lavender

(57) ABSTRACT

A dressing for negative pressure wound therapy includes an absorbent layer comprising a gelling absorbent material for absorbing exudate, a peripheral adhesive skin contact layer comprising a hydrocolloid adhesive and defining a window through which the absorbent layer is able to contact a wound, and a cover layer that is water impermeable and air permeable. The cover layer defines an aperture to be used with a pump assembly to provide negative pressure to a wound site.

29 Claims, 3 Drawing Sheets

(56) References Cited

U.S. PATENT DOCUMENTS

| | | |
|---|---|---|
| 10,463,773 B2 | 11/2019 | Haggstrom et al. |
| 10,470,933 B2 | 11/2019 | Riesinger |
| 10,470,936 B2 | 11/2019 | Wohlgemuth et al. |
| 10,471,122 B2 | 11/2019 | Shi et al. |
| 10,471,190 B2 | 11/2019 | Locke et al. |
| 10,478,345 B2 | 11/2019 | Barta et al. |
| 10,478,346 B2 | 11/2019 | Knutson |
| 10,478,394 B2 | 11/2019 | Yu |
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Laurensou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 2006/0155260 A1 | 7/2006 | Blott et al. |
| 2006/0172000 A1 | 8/2006 | Cullen et al. |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2009/0234307 A1 | 9/2009 | Vitaris |
| 2009/0259203 A1 | 10/2009 | Hu et al. |

(56) References Cited

U.S. PATENT DOCUMENTS

| | | |
|---|---|---|
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0125233 A1 | 5/2010 | Edward S. et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0208145 A1* | 8/2011 | Zhang .................. A61F 13/534 604/368 |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2012/0071845 A1 | 3/2012 | Hu et al. |
| 2012/0130332 A1* | 5/2012 | Cotton ................ A61F 13/0203 604/368 |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1* | 8/2014 | Von Wolff ............. A61L 15/26 604/369 |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollet et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0231858 A1* | 8/2015 | van Neer .................. B32B 7/14 428/201 |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1* | 2/2018 | Tunius ................ C08G 18/6229 |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1* | 5/2019 | Bishop .............. A61F 13/00055 |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |

(56) References Cited

U.S. PATENT DOCUMENTS

| | | |
|---|---|---|
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | MacPhee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | MacPhee et al. |
| 2019/0388589 A1 | 12/2019 | MacPhee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0095620 A1 | 3/2020 | Kellar et al. |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |

(56) References Cited

U.S. PATENT DOCUMENTS

| | | |
|---|---|---|
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0230283 A1 | 7/2020 | Yang et al. |
| 2020/0237562 A1 | 7/2020 | Rice et al. |
| 2020/0237564 A1 | 7/2020 | Hammond et al. |
| 2020/0237816 A1 | 7/2020 | Lait |
| 2020/0246190 A1 | 8/2020 | Luckemeyer et al. |
| 2020/0246191 A1 | 8/2020 | Lu et al. |
| 2020/0246194 A1 | 8/2020 | Gonzalez et al. |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0253788 A1 | 8/2020 | Rehbein et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0269028 A1 | 8/2020 | Hegg |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289326 A1 | 9/2020 | Nielsen et al. |
| 2020/0289327 A1 | 9/2020 | Hansen et al. |
| 2020/0289328 A1 | 9/2020 | Luckemeyer et al. |
| 2020/0289346 A1 | 9/2020 | Hansen et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306092 A1 | 10/2020 | Rehbein et al. |
| 2020/0306094 A1 | 10/2020 | Kushnir et al. |
| 2020/0306426 A1 | 10/2020 | Rice et al. |
| 2020/0306428 A1 | 10/2020 | Ingram et al. |
| 2020/0306430 A1 | 10/2020 | Rehbein et al. |
| 2020/0315853 A1 | 10/2020 | Waite |
| 2020/0315854 A1 | 10/2020 | Simmons et al. |
| 2020/0315894 A1 | 10/2020 | Churilla et al. |
| 2020/0316271 A1 | 10/2020 | Lin |
| 2020/0316272 A1 | 10/2020 | Simpson |
| 2020/0316273 A1 | 10/2020 | Hegg |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |

FOREIGN PATENT DOCUMENTS

| | | |
|---|---|---|
| EP | 3569260 A1 | 11/2019 |
| EP | 3643328 A1 | 4/2020 |
| EP | 3643330 A1 | 4/2020 |
| EP | 3643331 A1 | 4/2020 |
| EP | 3669838 A1 | 6/2020 |
| EP | 3669843 A1 | 6/2020 |
| EP | 3669844 A1 | 6/2020 |
| GB | 2579211 A | 6/2020 |
| GB | 2579368 A | 6/2020 |
| WO | 2005018543 A2 | 3/2005 |
| WO | 2011121394 A1 | 10/2011 |
| WO | 2011135284 A1 | 11/2011 |
| WO | 2011144888 A1 | 11/2011 |
| WO | 2013015827 A2 | 1/2013 |
| WO | 2013126049 A1 | 8/2013 |
| WO | 2014014842 A1 | 1/2014 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |

(56) References Cited

FOREIGN PATENT DOCUMENTS

| | | |
|---|---|---|
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |
| WO | 2020070231 A1 | 4/2020 |
| WO | 2020074512 A1 | 4/2020 |
| WO | 2020078993 A1 | 4/2020 |
| WO | 2020079009 A1 | 4/2020 |
| WO | 2020079330 A1 | 4/2020 |
| WO | 2020081259 A1 | 4/2020 |
| WO | 2020081391 A1 | 4/2020 |
| WO | 2020092598 A1 | 5/2020 |
| WO | 2020136555 A1 | 7/2020 |
| WO | 2020141059 A1 | 7/2020 |
| WO | 2020144347 A1 | 7/2020 |
| WO | 2020150548 A1 | 7/2020 |
| WO | 2020159675 A1 | 8/2020 |
| WO | 2020159677 A1 | 8/2020 |
| WO | 2020159678 A1 | 8/2020 |
| WO | 2020159823 A1 | 8/2020 |
| WO | 2020159859 A1 | 8/2020 |
| WO | 2020159892 A1 | 8/2020 |
| WO | 2020161086 A1 | 8/2020 |
| WO | 2020173665 A1 | 9/2020 |
| WO | 2020173760 A1 | 9/2020 |
| WO | 2020174264 A1 | 9/2020 |
| WO | 2020174510 A1 | 9/2020 |
| WO | 2020182887 A1 | 9/2020 |
| WO | 2020185810 A1 | 9/2020 |
| WO | 2020197759 A1 | 10/2020 |
| WO | 2020197760 A1 | 10/2020 |
| WO | 2020198484 A1 | 10/2020 |
| WO | 2020201879 A1 | 10/2020 |
| WO | 2020213998 A1 | 10/2020 |

* cited by examiner

NEGATIVE PRESSURE WOUND DRESSING

BACKGROUND

The subject matter disclosed herein relates generally to negative pressure dressings and to negative pressure tissue treatment devices having negative pressure dressings and, more particularly, to dressings that can be used with a source of negative pressure to deliver negative pressure therapy. Such dressings are suitable for the treatment of a variety of wounds including chronic and acute types, including infected wounds, venous ulcers, diabetic ulcers, burns, surgical wounds and the like.

Clinical studies and practice have shown that providing a negative pressure in proximity to a tissue site augments and accelerates the growth of new tissue at the tissue site. The applications of this phenomenon are numerous, but one particular application of negative pressure involves treating wounds. This treatment (frequently referred to in the medical community as "negative pressure wound therapy," "reduced pressure therapy," or "vacuum therapy") provides numerous benefits, including drawing out fluid from the wound, migration of epithelial and subcutaneous tissues, improved blood flow, and micro-deformation of tissue at the wound site. These benefits result in increased development of granulation tissue and faster healing times, while also helping to reduce the level of scar formation. Typically, negative pressure is applied by a reduced pressure source to tissue through a porous pad or other manifold device that is sealed to a patient's skin around the periphery of a wound or other tissue for which such treatment is prescribed. The porous pad includes cells or pores that are capable of distributing reduced pressure to the tissue and channeling fluids that are drawn from the tissue. The porous pad often is incorporated into a dressing having other components that facilitate treatment.

In the administration of negative pressure wound therapy, the negative pressure may be applied continuously or intermittently, depending on the type of wound or other tissue being treated and the clinical objectives. The dressing can be changed periodically, such as, for example, one, two, or three times per week (or as needed). The terms "reduced pressure" and "negative pressure" refer to a pressure that is below normal atmospheric pressure.

To enable a prolonged application of topical negative pressure, powered systems, which include a vacuum generation source such as a pump, have been developed. Many of these systems, however, are not convenient for users as they can be large, heavy, noisy, uncomfortable, and not simple for users to apply and operate correctly. Such systems also rely on an outside power or vacuum source to create the prescribed negative pressure conditions.

Negative pressure wound and tissue treatments and other advanced technical interventions are becoming more prevalent given the occurrence of both the aging population, as well as the increasingly compromised patient populations. This trend looks set to continue. In wound care, healthcare professionals are now more likely to encounter wounds that are difficult to manage with a multitude of complex healing problems.

While several approaches have been used in the application of negative pressure therapy for the management of wounds, these suffer from multiple issues. For example, one problem with negative pressure wound dressings in the prior art is that they often experience leaks around the dressing periphery. Relatedly, negative pressure wound dressings that experience leaks require more powerful pumps, which in turn require substantially greater inputs of energy, typically electrical energy, to maintain an acceptable amount of pressure reduction at the wound site. Another problem with such dressings relate to the dressing's inability to absorb and retain acceptable quantities of drainage and exudate from the wound site to promote an adequate environment for healing. Moreover, many prior art negative pressure wound dressings are provided as a set of multiple parts or components that require assembly via multiple application steps at the time the dressing is being applied over the wound, which often results in improper applications of the dressing and/or inoperability of the device. All of these problems detract from the effectiveness of the prescribed negative pressure wound therapy, resulting in a suboptimal wound healing environment.

There remains a need for negative pressure wound dressings that are simple to apply to a wound site, that are provided in the form of a unitary dressing construct and that provide improved sealing for maintenance of acceptable negative pressure at the wound site with decreased power requirements. The present disclosure addresses these needs and provides other benefits and advantages.

SUMMARY

The present disclosure provides negative pressure wound dressings, and devices that include negative pressure wound dressings. In one aspect of the disclosure, there is provided a unitary negative pressure wound dressing construct that includes: (i) an absorbent layer having a first surface for contacting a wound and a second surface opposite the first surface, the absorbent layer comprising a gelling absorbent material and having a perimeter border, (ii) a cover layer having a first surface facing the absorbent layer and a second surface opposite the first surface, wherein the cover layer has a perimeter border having dimensions greater than the dimensions of the absorbent layer perimeter such that the perimeter border of the cover layer extends beyond the perimeter border of the absorbent layer, and (iii) a peripheral adhesive skin contact layer attached to the first surface of the absorbent layer adjacent the perimeter border of the absorbent layer, wherein the peripheral adhesive skin contact layer defines a window through which the absorbent layer is able to contact the wound, and wherein the peripheral adhesive skin contact layer comprises a hydrocolloid adhesive. In some embodiments, the dimensions of the perimeter border of the absorbent layer are greater than dimensions of a wound to be covered by the dressing. In some embodiments, wherein the cover layer is water impermeable. In some embodiments, the cover layer is water impermeable and air and vapour permeable. In some embodiments, the peripheral adhesive skin contact layer has a perimeter border having dimensions greater than the dimensions of the absorbent layer perimeter such that the perimeter border of the peripheral adhesive skin contact layer extends beyond the perimeter border of the absorbent layer. In some embodiments, the perimeter border of the cover layer and the perimeter border of the peripheral skin contact layer are bonded together to form a seal. In some embodiments, the peripheral adhesive skin contact layer is operable to adhere to skin surrounding a wound. In some embodiments, the cover layer defines an aperture configured for connection to a source of negative pressure.

In some embodiments, the peripheral adhesive skin contact layer and the cover layer are operable to form an air-tight seal between the absorbent layer and an external environment of the dressing when the dressing is applied over a wound and a source of negative pressure is sealingly connected to the aperture. In some embodiments, the peripheral adhesive skin contact layer has a thickness of from about 0.1 mm to about 5 mm. In some embodiments, the peripheral adhesive skin contact layer has a width of from about 2 cm to about 6 cm.

In some embodiments, the dressing further includes a first bonding layer positioned between the absorbent layer and the cover layer. In some embodiments, the first bonding layer comprises a layer of hydrocolloid adhesive. In some embodiments, the first bonding layer has a thickness of from about 0.2 mm to about 2 mm.

In some embodiments, the dressing further includes a structural layer corresponding to the peripheral adhesive skin contact layer and having a first surface bonded to the peripheral adhesive skin contact layer, and a second bonding layer corresponding to the peripheral adhesive skin contact layer and positioned in contact with a second surface of the structural layer that is opposite the first surface of the structural layer. In some embodiments, the structural layer is positioned between, and sealingly bonded to, the peripheral adhesive skin contact layer and the second bonding layer. In some embodiments, the second bonding layer is sealingly bonded to a continuous portion of the first surface of the absorbent layer that is adjacent the full perimeter border of the absorbent layer. In some embodiments, the peripheral adhesive skin contact layer, the second bonding layer and the cover layer are operable to form an air-tight seal between the absorbent layer and an external environment of the dressing when the dressing is applied over a wound and a source of negative pressure is sealingly connected to the aperture. In some embodiments, the structural layer comprises a polyurethane film. In some embodiments, the second bonding layer has a thickness of from about 0.2 mm to about 2 mm.

In some embodiments, the dressing further includes a first bonding layer positioned between the absorbent layer and the cover layer, a structural layer corresponding to the peripheral adhesive skin contact layer and having a first surface bonded to the adhesive skin contact layer, and a second bonding layer corresponding to the peripheral adhesive skin contact layer and positioned in contact with a second surface of the structural layer that is opposite the first surface of the structural layer. In some embodiments, the structural layer is positioned between, and sealingly bonded to, the peripheral adhesive skin contact layer and the second bonding layer. In some embodiments, the second bonding layer is sealingly bonded to a continuous portion of the first surface of the absorbent layer that is adjacent the full perimeter border of the absorbent layer.

In some embodiments, the gelling absorbent material comprises a gel-forming fiber or filament. In some embodiments, the gel-forming fiber or filament comprising chemically-modified cellulose, alginate, carboxymethyl cellulose, or combinations thereof. In some embodiments, the absorbent layer comprises stitches. In some embodiments, the absorbent layer further comprises an antimicrobial agent. In some embodiments, the cover layer comprises a member selected from the group consisting of a polyurethane (PU), a polyvinyl chloride (PVC), a silicone elastomer, a fluoropolymer, and combinations thereof.

In some embodiments, the dressing further includes a source of negative pressure sealingly connected to the aperture and in fluid communication with the absorbent layer. In some embodiments, the source of negative pressure comprises a pump connected to the aperture. In some embodiments, the pump is connected to the aperture with a conduit. In some embodiments, the dressing further includes a connector attached to the cover layer over the aperture and configured for connection to a conduit to communicate negative pressure from the conduit to the wound through the aperture. In some embodiments, the connecter comprises polyurethane or polyvinylchloride. In some embodiments, the connecter comprises a change indicator.

In some embodiments, the dressing further includes a negative pressure distribution layer positioned between the absorbent layer and the cover layer. In some embodiments, the negative pressure distribution layer comprises an open cell foam layer. In some embodiments, the open cell foam layer is hydrophobic.

In another aspect of the disclosure, there is provided a disposable negative pressure wound therapy device that includes a disposable pump for generating negative pressure, and a dressing according to any of the embodiments disclosed herein for covering and protecting a wound, wherein the cover layer defines an aperture connected to the pump. In some embodiments, the disposable pump is a battery operated pump. In some embodiments, the device further includes a conduit defining a lumen that provides fluid communication between the pump and the aperture defined in the cover layer of the dressing, whereby operation of the pump creates negative pressure at the site of a wound when the dressing is affixed over the wound by pressure sealing the peripheral adhesive skin contact layer to skin surrounding the wound.

Further features, characteristics and embodiments of the present disclosure will be apparent from the detailed description herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

Figure 1:
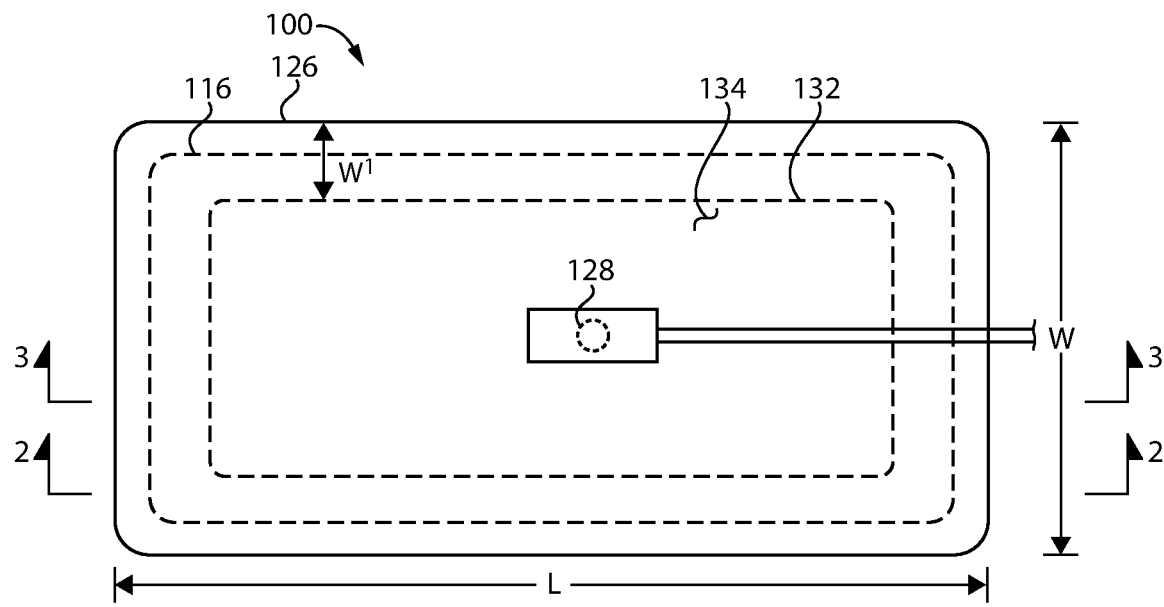
FIG. 1 illustrates a schematic top view one dressing embodiment according to the disclosure.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein.

DETAILED DESCRIPTION

For the purposes of promoting an understanding of the principles of the invention, reference will now be made to the embodiments described herein and illustrated in the Figures and specific language will be used to describe the same. The embodiments of the present application described below are not intended to be exhaustive or to limit the teachings of the present application to the precise forms disclosed in the following detailed description. Rather, the embodiments are chosen and described so that others skilled in the art may appreciate and understand the principles and practices of the present application. It will therefore be understood that no limitation of the scope of the invention is intended by the description of specific embodiments. Any alterations and further modifications in the described embodiments, and any further applications of the principles of the invention as described herein are contemplated as would normally occur to one skilled in the art to which the invention relates.

Problems and challenges associated with negative pressure wound dressings in the prior art, such as poor seals, complex on-site assembly and the like are addressed by the present disclosure, which provides new negative pressure wound dressing constructs that feature unitary construction with strong seals and excellent fluid absorption characteristics.

One aspect of the disclosure is a dressing that includes an absorbent layer comprising a gelling absorbent material, a cover layer composed of a water impermeable and air and vapour permeable material overlying the absorbent layer, and a peripheral adhesive skin contact layer situated beneath the peripheral border of the absorbent layer to sealingly affix the dressing to a patient's skin. As used in the above sentence, the term "beneath" means "on the opposite side from the skin cover layer." The peripheral adhesive skin contact layer comprises a hydrocolloid adhesive. The cover layer defines an aperture configured for connection to a source of negative pressure.

The dressings disclosed herein are particularly suitable for use in vacuum and/or negative pressure wound therapy, but can alternatively be used in other contexts as well, including but not limited to use in other exudate or fluid producing instances.

Vacuum wound therapy can be used for the treatment of a multitude of wound types, including but not limited to, acute wounds (such as, following fasciotomy or other surgeries), chronic wounds (such as pressure ulcers, trophic and vascular ulcers), and the management of complex soft tissue injuries (such as, open abdomen (laparotomy)).

Certain Terminologies

Unless defined otherwise, all technical and scientific terms used herein have the same meaning as is commonly understood by one of skill in the art to which the subject matter of this disclosure belongs. Moreover, it should be understood that when certain values and ranges are recited herein in connection with various embodiments of the present teachings, all values and ranges which fall between such listed values and ranges are intended to be encompassed by the present teaching unless explicitly stated otherwise. Finally, although specific methods and materials are described herein with respect to certain representative aspects of the present disclosure, it should be understood and appreciated that other methods and materials similar or equivalent to those described herein can be used in the practice or testing of the present application without straying from the intended scope of this disclosure.

It is to be understood that the following general description and the following examples are explanatory only and are not restrictive of any subject matter claimed. It is also to be understood that, while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the terms "comprising," "including" and "having," as well as other forms, such as "comprise," "comprises," "comprised," "include," "includes," "included," "have" and "has" are inclusive and not limiting, and therefore specify the presence of stated features, integers, steps, operations, elements, and/or components, but do not preclude the presence or addition of one or more other features, integers, steps, operations, elements, components, and/or groups thereof. The method actions, processes, and operations described herein are not to be construed as necessarily requiring their performance in the particular order discussed or illustrated, unless specifically identified as an order of performance. It is also to be understood that additional or alternative actions or operations may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed herein could be termed a second element, component, region, layer or section without departing from the teachings of the example embodiments.

As used herein, ranges and amounts can be expressed as "about" a particular value or range. About also includes the exact amount. For example, "about 5 µL" means "about 5 µL" and also "5 µL." Generally, the term "about" includes an amount that would be expected to be within experimental error. The term "about" includes values that are within 10% less to 10% greater of the value provided. For example, "about 50%" means "between 45% and 55%." Also, by way of example, "about 30" means "between 27 and 33."

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human.

The term "exudate" refers to any fluids produced by a wound that may be secreted from the wound.

The term "periwound" refers to the area directly bordering the wound area itself. The term "periskin" refers to the skin area directly bordering the wound area itself.

The terms "negative pressure" and "reduced pressure" as used herein generally refer to a pressure less than the ambient pressure at a tissue site that is being subjected to treatment. In most cases, this reduced pressure will be less than the atmospheric pressure at which the patient is located. Alternatively, the reduced pressure may be less than an hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum.

As used herein, the term "moldable" refers to an elastic, deformable property and ability to conform and/or form a seal. The moldable materials of various embodiments disclosed herein may be differentiated from stretchable and flexible materials. The term, "moldable" can encompass the properties of malleability and ductility. The absolute shape change of a moldable material may be controlled by an external resistive element resulting in conformance to a complimentary feature.

As used herein, the term "flexible" refers to the elastic deformation of a structure under an external force. Upon removal of the external force the structure will substantially return to its original (previous) geometry. Measurement of flexibility can be quantified in linear displacement (μm, mm, cm, m), e.g., original length/diameter and flexed length/diameter. The second moment of area influences the deformation experienced by the body. A device which is moldable can also have the property of flexibility. Flexibility is desirable in dressings. Skin flexes during the movement and activities of daily living, especially in areas over joint tissues. Rigid systems would not be able continually adapt to the skin flexibility. However, flexible devices are capable of continually adapting to the skin and mucosal membranes flexibility.

The general term "adhesive," as used herein, refers to layers, fabrics, strips, laminates, barriers and materials that are used to promote adherence of a dressing to the skin and/or promote a seal between layers of the dressing to one another, thereby preventing undesirable leakage of effluent and providing an effective environment for application of negative pressure.

A Dressing

Several representative embodiments of dressings suitable for use in connection with negative pressure wound therapy are described herein. First with reference to FIGS. 1-3, dressing 100 includes absorbent layer 110, cover layer 120 and peripheral adhesive skin contact layer 130. While the dressings disclosed herein can have a wide variety of shapes and sizes, for the sake of convenient description, dressing 100 depicted in FIGS. 1-3 has a generally rectangular shape with a length dimension L and a width dimension W. Absorbent layer 110 has first surface 112 for contacting a wound and second surface 114 opposite first surface 112, and has perimeter border 116 preferably having dimensions greater than the dimensions of a wound to be covered by dressing 100. Cover layer 120 has first surface 122 facing absorbent layer 110 and has second surface 124 opposite first surface 122, and has perimeter border 126 that extends beyond perimeter border 116 of absorbent layer 110. As such, perimeter border 126 has dimensions greater than dimensions of perimeter border 116 of absorbent layer 110. Peripheral adhesive skin contact layer 130 is attached to first surface 112 of absorbent layer 110 adjacent its perimeter border 116. Peripheral adhesive skin contact layer 130 has an inner edge 132 that defines a window 134 through which first surface 112 of absorbent layer 110 is able to contact a wound over which dressing 100 is applied.

In some embodiments, first surface 122 of cover layer 120 is bonded to first surface 114 of absorbent layer by an adhesive. In other embodiments, at least a portion of cover layer 120 adjacent its perimeter 126 is bonded to a portion of absorbent layer 110 adjacent its perimeter 116. In some embodiments, first surface 122 of cover layer 120 is bonded to first surface 114 of absorbent layer by positioning a bonding layer between absorbent layer 110 and cover layer 120. In some embodiments the bonding layer comprises an adhesive. In some embodiments, the bonding layer comprises a layer of hydrocolloid adhesive.

Dressing 100 is configured to be held in place over a wound by peripheral skin contact layer 130, which extends around the border of the dressing and defines a window therethrough. Peripheral adhesive skin contact layer 130 is composed of a material that is capable of durably and strongly adhering to skin to form a seal. The durability of the dressing's adherence to a patient's skin is an important factor in the prevention of an unacceptable level of leakage during application of negative pressure wound therapy. A person of ordinary skill understands that such durability is directly proportional to the properties of the composition used to make the peripheral skin contact layer 130, which impacts the strength of adherence between the peripheral adhesive skin contact layer and underlying skin, and also is directly proportional to the width $W^1$ of peripheral adhesive skin contact layer 130. In one embodiment, peripheral adhesive skin contact layer 130 has a width of from about 1 cm to about 10 cm. In another embodiment, peripheral adhesive skin contact layer 130 has a width of from about 2 cm to about 6 cm. In still another embodiment, peripheral adhesive skin contact layer 130 has a width of from about 2 cm to about 5 cm Peripheral adhesive skin contact layer 130 and cover layer 120 are operable to form an air-tight seal between the absorbent layer and an external environment of dressing 100 when dressing 100 is applied over a wound and a source of negative pressure is sealingly connected to aperture 128.

Figure 2:
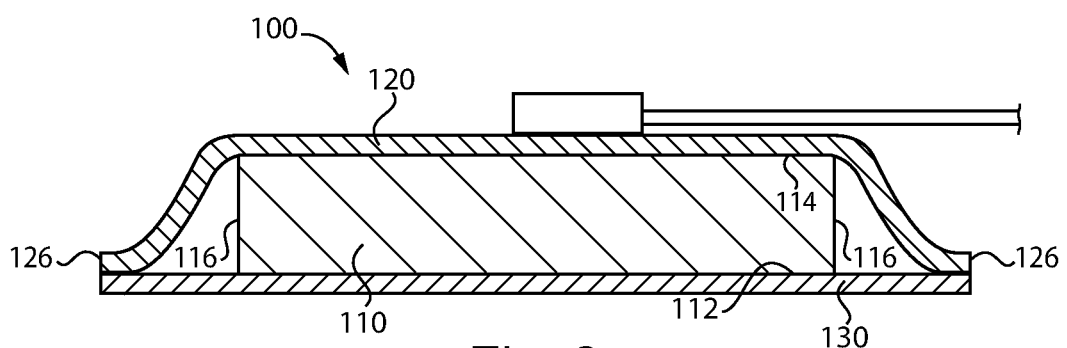
FIG. 2 illustrates a cross-sectional side view of the dressing embodiment shown in FIG. 1.
Figure 3:
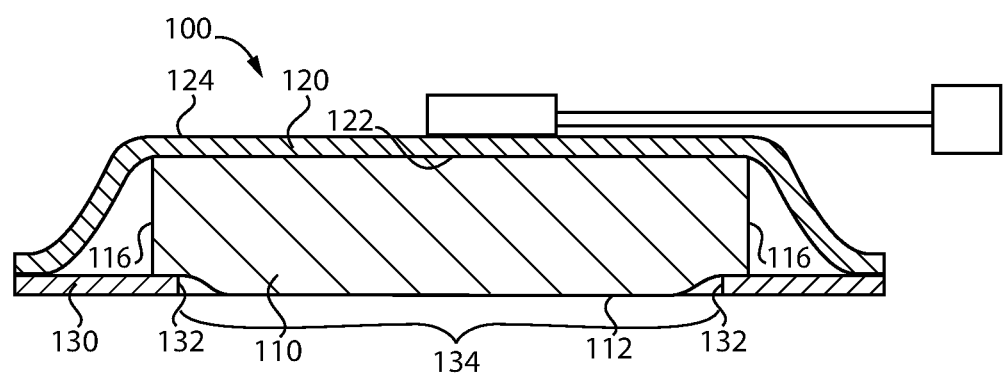
FIG. 3 illustrates another cross-sectional side view of the dressing embodiment shown in FIG. 1.

When dressing 100 (or any other dressing disclosed herein) is manufactured, a removable film, referred to herein as a "removable backing" (not shown) may be adhered to an outer surface (also referred to as "bottom surface") of peripheral adhesive skin contact layer 130, which removable backing is to be removed before use of dressing 100. With reference to FIGS. 1-3, in one embodiment the removable backing may be adhered to the outer surface of peripheral adhesive skin contact layer 130 opposite the side of peripheral adhesive skin contact layer 130 that faces toward cover layer 126. The removable backing, which may include multiple sections and may include folded grip sections, is removable from peripheral adhesive skin contact layer 130 before use of dressing 100. Thus, in a preferred embodiment the removable backing protects peripheral adhesive skin contact layer 130 when the removable backing is adhered to peripheral adhesive skin contact layer 130, but when the removable backing is removed from peripheral adhesive skin contact layer 130 for use of dressing 100 the outer surface of peripheral adhesive skin contact layer 130 is exposed and able to releasably secure dressing 100 to the skin of a user to provide a deformable pressure seal around the wound. The removable backing in some embodiments is also sized to cover the entire bottom surface of dressing 100, including the bottom surface of peripheral adhesive skin contact layer 130 and also any exposed portion of any other layer, such as, for example, the portion of absorbent layer 110 that is exposed through window 134.

Absorbent Layer

Absorbent layer 110 is composed of a gelling absorbent material. The gelling absorbent material preferably is capable of absorbing exudate from a wound and allowing passage of fluid through it. Absorbent layer 110 may have an open weave structure with pockets available for fluid absorption. In other embodiments, the absorbent layer may be nonwoven, knitted or formed of a tight weave. In some embodiments, the absorbent layer is a nonwoven. The absorbent layer can expand upon absorption of exudate or other fluid produced from the wound site.

In some embodiments, the absorbent layer comprises a gel-forming fiber, filament, or agent. In some embodiments, the gel-forming fiber or filament is chemically-modified cellulose, alginate, or carboxymethyl cellulose, or a combination thereof. In some embodiments, the gel-forming fiber is carboxymethyl cellulose. The absorbent layer also can include other absorbent materials such as, for example, polyacrylate, polyacrylate fibers, bi-component superabsorbent fibers, air laid nonwovens, needlefelt nonwovens, thermobonded nonwovens and foams.

Some formulations of the absorbent layer contain an alginate to increase absorption capabilities. The active surface of the absorbent layer can be coated with a cross-linked adhesive mass containing a dispersion of gelatin, pectin and/or carboxymethyl cellulose together with other polymers. In contact with traditional dressings, the polysaccharides and other polymers absorb water and swell, forming a gel. The moist conditions produced under the dressing are intended to promote fibrinolysis, angiogenesis and wound healing, without causing softening and breaking down of tissue.

Absorbent layer 110 preferably comprises gel forming fibres. By gel forming is meant hygroscopic fibres which upon the uptake of wound exudate become moist slippery or gelatinous and thus reduce the tendency for the surrounding fibres to adhere to the wound. The gel forming fibres can be of the type which retain their structural integrity on absorption of exudate or can be of the type which lose their fibrous form and become a structureless gel. The gel forming fibres are preferably spun sodium carboxymethylcellulose fibres, chemically modified cellulosic fibres, pectin fibres, alginate fibres, chitosan fibres, hyaluronic acid fibres, or other polysaccharide fibres or fibres derived from gums. The gel forming fibres are preferably sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The gel forming fibres are preferably chemically modified cellulosic fibres in the form of a fabric and in particular carboxymethylated cellulose fibres as described in PCT WO00/01425 to Azko Nobel UK Ltd. The cellulosic fibres preferably have a degree of substitution of at least 0.05 carboxymethyl groups per glucose unit. In another embodiment, the cellulosic fibres have a degree of substitution of from about 0.12 to about 0.35 as measured by IR spectroscopy (as defined in WO 00/01425). In another embodiment, the cellulosic fibres have a degree of substitution of from about 0.20 to about 0.30 and are made by carboxymethylating a woven, knitted, or nonwoven cellulosic fabric such that the absorbency is increased. The gel forming fibres preferably have an absorbency of at least 2 grams 0.9% saline solution per gram of fibre (as measured by the free swell method).

Preferably the gel forming fibres have an absorbency of at least 10 g/g as measured in the free swell absorbency method, more preferably, between 15 g/g and 25 g/g.

The gelling absorbent material can be made in accordance with the disclosure of WO 93/12275, which describes the production of various absorbent carboxymethylated cellulosic products that are capable of absorbing many times their own weight of water. This causes the carboxymethylated fibres to form a gel. WO 94/16746 and WO 00/01425 describe the use of carboxymethylated Lyocell materials in wound dressings where the advantages of gel formation in preventing adherence and therefore reducing wound damage and pain on removal are described.

Carboxymethylation can be achieved, for example, by sequential or simultaneous treatment of the cellulosic material with a strong alkali, such as aqueous sodium hydroxide, and monochloroacetic acid or a salt thereof. The appropriate reaction conditions will depend upon the composition of the fabric and the degree of carboxymethylation required and will be readily apparent to the person skilled in the art. They may be identical or similar to those described in WO 93/12275, WO 94/16746 or WO 00/01425. Desirably the carboxymethylation is carried out in the presence of industrial methylated spirits (IMS), and IMS is preferably also used in a subsequent washing step, suitably along with water, as a cleaner and steriliser. The degree of carboxymethylation is desirably such that upon absorption of exudate the fibres at the skin-contacting surface of the bandage form a gel.

In some embodiments, absorbent layer 110 comprises carboxymethylated cellulose fibres formed into a fabric. In other embodiments, absorbent layer 110 comprises two or more layers of fabric comprising carboxymethylated cellulose fibres. In one embodiment, absorbent layer 110 comprises from about two to about ten layers of fabric comprising carboxymethylated cellulose fibres. In another embodiment, absorbent layer 110 comprises from about two to about eight layers of fabric comprising carboxymethylated cellulose fibres.

In one embodiment in which absorbent layer 110 comprises one or more layers of fabric comprising carboxymethylated cellulose fibres, absorbent layer 110 further comprises stitching to increase the tensile strength and/or the resilience of dressing 100. In an absorbent layer that includes more than one layer of fabric comprising carboxymethylated cellulose fibres, the stitching can be present in only one or in more than one fabric layer. In one embodiment stitching is present in the fabric layer that is positioned to contact the wound in use of dressing 100.

Stitching contemplated by this disclosure can include inelastic threads or yarns and/or resilient thread or yarn. WO 2007/003905 describes dressings in which stitching is used to increase the tensile strength of dressings, which are particularly suitable for use in dressing burns. U.S. Pat. No. 10,117,783 describes dressings in which stitching is used to increase the resilience of dressings, which are particularly suitable for use in dressings placed on body positions were movement occurs, such as joints (e.g., elbows, knees, hips, etc.) or abdomen.

By resilient is meant that the yarn or thread is able to extend and contract to its former shape. The gathers in the absorbent layer formed by the resilient thread or yarn, enable the absorbent layer to extend and contract with movement so that when, for example, the patient's leg is bent the dressing stretches and when the leg is straightened, the dressing recovers its former size. This resilience means that the absorbent layer maintains close conformability with the wound during movement of the patient. It also means that the dressing has a reduced tendency to delaminate during wear. Having the ability to stretch means that there is less movement between the dressing and the patient which enables a more durable seal between the dressing and the patient's underlying skin.

Preferably the absorbent layer further comprises lines of longitudinal warp stitches formed from an inelastic thread which stitching is longitudinal in that it is generally parallel to the long dimension of the absorbent layer. The warp stitches are preferably made in the absorbent layer after it has been formed.

The inelastic warp stitching preferably passes through the whole thickness of the absorbent layer and is visible on both sides. The absorbent layer preferably comprises two or more layers of fabric that are layered together and stitch bonded with lines of longitudinal inelastic warp stitches. The resilient thread is preferably woven in between the stitches of the inelastic warp stitching and in between the sheets of fabric. By having two layers of fabric it is possible to hold the resilient thread or yarn out of direct contact with the wound.

The resilient thread gathers the absorbent layer and enables it to elongate and then return to shape. The resilient thread can be stitched through the absorbent layer to gather the dressing or woven through a separate line of inelastic warp stitches. The resilient thread can be stitched through the absorbent layer in lines of longitudinal stitches 1 mm to 10 mm apart, more preferably 2 mm to 5 mm apart. The resilient thread is preferably applied to the absorbent layer after the absorbent layer has been formed.

The lines of inelastic warp stitching may be from 1 mm to 10 mm apart and preferably from 2 mm to 5 mm apart. The lines of inelastic stitching are typically crocheted or knitted and have the appearance of a chain stitch but other stitch patterns may also be used. Preferably, the lines of resilient stitching gather the absorbent layer so that the absorbent layer is able to elongate by 25% to 85%, more preferably 35% to 75% and most preferably 40% to 70% and then recover even when the absorbent layer is hydrated. More preferably, the lines of warp stitching are made in a yarn or thread such as nylon or polyester or Tencel® (Lenzing Aktiengesellschaft) or any thread which is strong and easily processed. The resilient stitches are made in a resilient yarn such as an elastomeric yarn or Lycra or other yarn which has good stretch and recovery or an elastane yarn which is an elastomeric yarn with greater than 85% polyurethane such as Lycra® (The Lycra Company) or Spandex.

In one representative way of making absorbent layer 110, it is made from a non-woven roll made by forming a web of Lyocell which is then hydroentangled. The web is then carboxymethylated by sequential or simultaneous treatment of the cellulosic material with a strong alkali, monochloroacetic acid or a salt thereof. Two webs of the resulting fabric are then fed into a stitch bonding machine and stitched simultaneously with lines of longitudinal stitching in an inelastic yarn and a resilient yarn woven in between the stitches and so secured at the centre of the webs. The resilient yarn gathers the absorbent layer (not shown) and is carried by the inelastic stitch bonded yarn. The resulting layer has a basis weight of 350 gm$^{-2}$.

In another representative way of making absorbent layer 110, it is made from a tow of carboxymethyl cellulose filaments which has been needlefelted. Two webs of the needlefelted tow are fed into a stitch bonding machine and stitched simultaneously with lines of longitudinal stitching in inelastic yarn and with a resilient yarn woven in between the stitches and so secured at the centre of the webs.

In one embodiment, absorbent layer 110 is provided with fenestrations to aid the application of negative pressure to the wound and maintain the pathway for fluid from the wound, through the absorbent layer. Typically, however, fenestrations are only provided in internal absorbent layers. External absorbent layers, including those in direct contact with the wound, generally do not have mechanically added fenestrations, however, they do have openings between the fibres.

Absorbent layer 110 may comprise one or more medicaments. For example an antimicrobial agent, or an antibiotic, or an anaesthetic on an anti-inflammatory agent or a skin protective agent or an odour absorbing agent. In some embodiments, the absorbent layer comprises an antimicrobial agent that can inhibit the growth of gram negative bacteria and/or gram positive bacteria. The antimicrobial agent can kill microbes, inhibit microbes' growth cycle, or disrupt the formation of microbial biofilms. Antimicrobial agents inhibit the growth of bacteria and thus, promote healthy wound healing.

Cover Layer

Cover layer 120 may be any material that provides a fluid seal. A fluid seal is a seal adequate to maintain reduced pressure at a desired site given the particular reduced pressure source or subsystem involved. The cover layer may be, for example, an impermeable or semi-permeable, elastomeric material. For semi-permeable materials, the permeability must be low enough that for a given reduced-pressure source, the desired reduced pressure may be maintained. The cover layer may be waterproof. In some embodiments, the cover layer comprises polyester, polyurethane (PU), polyvinyl chloride (PVC), silicone elastomer, or fluoropolymers. In some embodiments, the cover layer may comprise polyester or polyurethane film.

Cover layer 120 is adapted to enable negative pressure to be applied at the wound and defines an aperture therethrough configured for connection to a source of negative pressure. In one embodiment, the aperture comprises a port configured for attachment to a conduit that is, in turn, configured for attachment to a source of negative pressure. The dressing provides a fluid pathway from the wound, through the absorbent layer and the aperture to the conduit. The port is preferably located in that part of the cover layer that overlies the absorbent layer but towards the periphery of the absorbent layer so that it is not directly in vertical alignment with the centre of the dressing (or the wound when in use). This assists in the spread of exudate across the full extent of the absorbent layer.

In one embodiment, cover layer 120 of dressing 100 is a bacterial and viral barrier layer which preferably resists the ingress of liquid and air but allows moisture vapour transmission. In this way the outer cover layer enhances the overall fluid handling capacity of the dressing by allowing for the escape of moisture vapour through the cover while enabling the application of negative pressure to the wound. The outer cover layer is for instance a layer having a MVTR of at least 10,000 gm$^{-2}$ per 24 hours or in the range of from 10,000 gm$^{-2}$ to 50,000 gm$^{-2}$ per 24 hours measured by the method described in BS EN 13726-2 2002 "Test methods for primary wound dressings Part 2 Moisture vapour transmission rate of permeable film dressings.". The cover layer may be in the form of a film of polyurethane, for example Epurex 92 T/129 manufactured by Covestro or Inspire 2350 manufactures by Coveris or Medifilm 426 manufactured by Mylan.

Peripheral Adhesive Skin Contact Layer

Peripheral adhesive skin contact layer 130 may be of the type comprising a homogenous blend of one or more water soluble hydrocolloids and one or more low molecular weight polyisobutylenes such as are described in EP-B-92999 incorporated herein by reference. The water soluble hydrocolloids may be selected from sodium carboxymethylcellulose, pectin, gelatine, guar gum, locust bean gum, karaya gum, and mixtures thereof. The polyisobutylenes may be selected from low molecular weight polyisobutylenes having a viscosity average molecular weight of from 36,000 to 58,000 (Florey). The peripheral adhesive skin contact layer is capable of absorbing exudate while maintaining adhesion of the dressing to the skin.

Alternatively the adhesive composition may comprise a homogeneous blend of one or more hydrocolloids, one or more low molecular weight polyisobutylenes, one or more styrene block copolymers, mineral oil, butyl rubber, a tackifier and small amounts of optional components. By selection of specific ranges of the amounts of the above listed components, an adhesive composition may be prepared having good adhesion to the skin and stretchability. Such compositions and the preparation therefore are disclosed in EP-B-130061.

Preferably the composition of peripheral adhesive skin contact layer 130 is such that the removal of an adhesive wound dressing is not traumatic to the patient. Preferably the peripheral adhesive skin contact layer ensures a secure application of the dressing whist still permitting non-traumatic removal. Non-traumatic dressing removal may be facilitated by using an adhesive which gels slightly upon interaction with a fluid. The gel formation aids dressing removal.

The term, "hydrocolloid adhesive," as used herein, refers to an adhesive material or substance that comprises a hydrocolloid. The formulation of these adhesives may be modulated to adjust physical properties of the material (e.g., its ability to create a vacuum seal, flexibility, breathability, comfort, size, etc.).

In some embodiments, the peripheral adhesive skin contact layer is at least 1%, at least 5%, at least 10%, at least 15%, at least 20%, at least 30%, at least 40%, or at least 50% w/w hydrocolloid.

Peripheral adhesive skin contact layer 130 is operable to provide a seal between the peripheral adhesive skin contact layer and the skin, thereby preventing exudate leakage.

In some embodiments disclosed herein, the peripheral adhesive skin contact layer has a thickness of from about 0.1 mm to about 5 mm. In other embodiments, the skin contact layer has a thickness of from about 0.15 mm to about 3 mm. In yet other embodiments, the skin contact layer has a thickness of from about 0.2 mm to about 2 mm.

Figure 4:
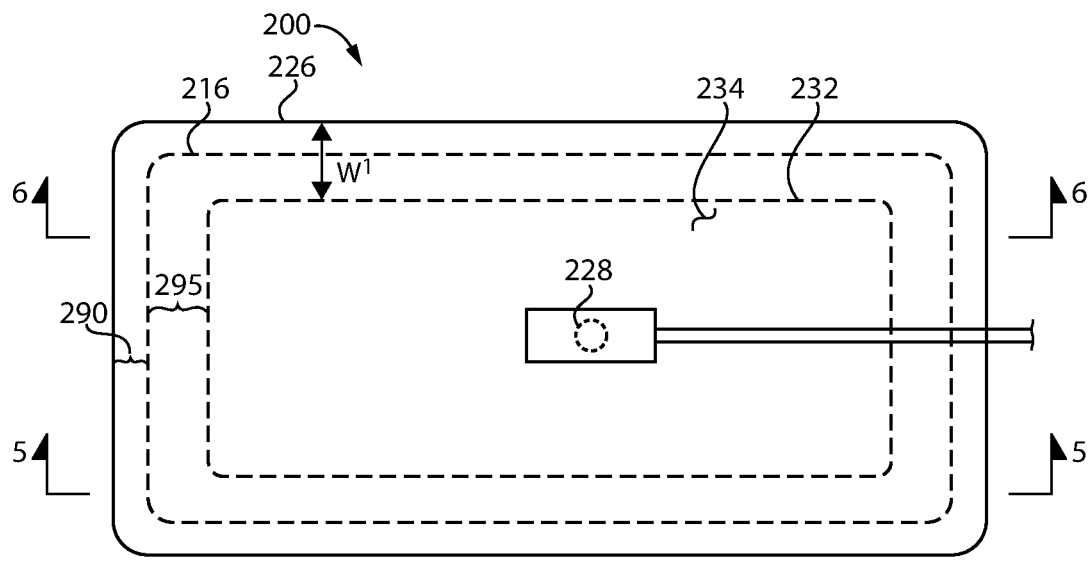
FIG. 4 illustrates a schematic top view another dressing embodiment according to the disclosure.
Figure 5:
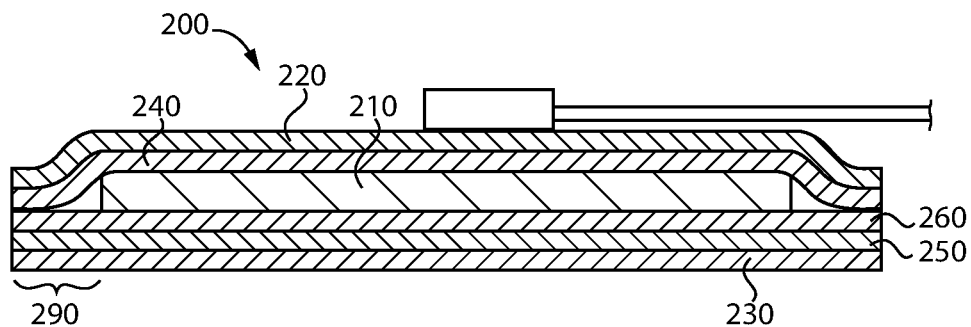
FIG. 5 illustrates a cross-sectional side view of the dressing embodiment shown in FIG. 4.
Figure 6:
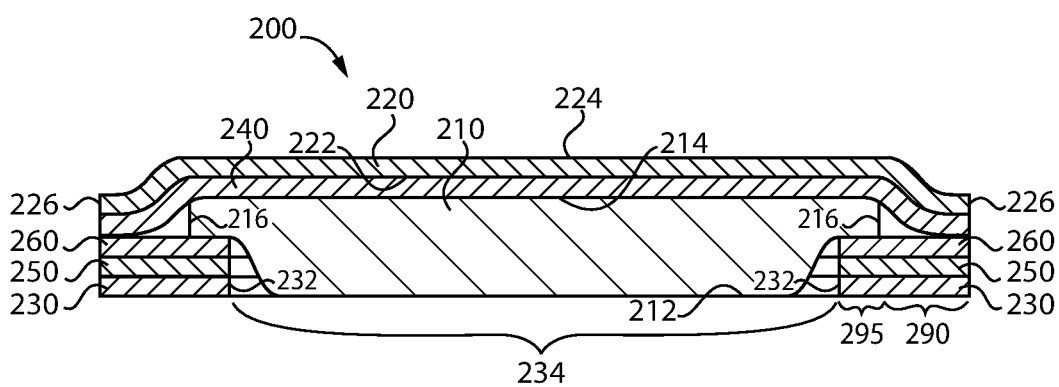
FIG. 6 illustrates another cross-sectional side view of the dressing embodiment shown in FIG. 4.

In other embodiments, additional structural layers and/or bonding layers are included in the dressing. With reference to FIGS. 4-6, dressing 200 includes many features corresponding to those of dressing 100, and also includes first bonding layer 240, reinforcing structural support layer 250 (also referred to as structural layer 250) and second bonding layer 260. First bonding layer 240 lies between cover layer 220 and absorbent layer 210 and operates to adhere cover layer 220 to absorbent layer 210. Structural layer 250 overlays peripheral adhesive skin contact layer 230 and functions as a scrim to add stability to peripheral adhesive skin contact layer 230. Structural layer 240 helps to reduce any tendency of peripheral adhesive skin contact layer 230 to delaminate on dressing removal. Second bonding layer 260 overlies structural layer 250 to bond structural layer 250 and the underlying peripheral adhesive skin contact layer 230 to absorbent layer 210. As shown most clearly in FIG. 6, second bonding layer 260 and structural layer 250 also define a window cut therefrom that coincide with window 234 in peripheral adhesive skin contact layer 230 to enable direct contact between absorbent layer 210 and an underlying wound.

Absorbent layer 210 has first surface 212 for contacting a wound and second surface 214 opposite first surface 212, and has perimeter border 216 having dimensions greater than the dimensions of a wound to be covered by dressing 200. Cover layer 220 has first surface 222 facing absorbent layer 210 and has second surface 224 opposite first surface 222, and has perimeter border 226 that extends beyond perimeter border 216 of absorbent layer 210. As such, perimeter border 226 has dimensions greater than dimensions of perimeter border 216 of absorbent layer 210. Between first surface 222 of cover layer 220 and second surface 214 of absorbent layer 210 is positioned first bonding layer 240. Between peripheral adhesive skin contact layer 230 and first surface 212 of absorbent layer 210 adjacent its perimeter border 216 are situated structural layer 250 and second bonding layer 260, oriented such that structural layer 250 is adjacent to, and bonded to, peripheral adhesive skin contact layer 230, and second bonding layer 260 is situated between structural layer 250 and first surface 212 of absorbent layer 210, thereby bonding structural layer 250 to absorbent layer 210 in the area of peripheral border 216 of absorbent layer 210. Peripheral adhesive skin contact layer 230 has an inner edge 232 that coincides with inner edges of structural layer 250 and second bonding layer 260, together defining a window 234 through which first surface 212 of absorbent layer 210 is able to contact a wound over which dressing 200 is applied.

As shown most clearly in FIGS. 5 and 6, in area 290 between perimeter borders 216 and 226, peripheral adhesive skin contact layer 230 is bonded to structural layer 250, which is bonded to second adhesive layer 260, which is bonded to first adhesive layer 240, which is bonded to cover layer 220. As shown most clearly in FIG. 6, in area 295 between area 290 and window 234, perimeter borders 216 in this sectional view lie between first bonding layer 240 and second bonding layer 260. With these layers bonded together as shown, when peripheral skin contact layer 230 is affixed to a patient's skin surrounding a wound, peripheral skin contact layer 230, structural layer 250, second bonding layer 260 and first bonding layer 240, together with cover layer 220 and the patient's skin, form an airtight seal around the perimeter of dressing 200, providing therein a sealed chamber in which the patient's wound is in fluid communication with absorbent layer 210 and with aperture 228 in cover layer 220.

Structural Layer

In some embodiments, structural layer 250 comprises a polymer selected from, but not limited to, polypropyleneoxide, polyurethane, polyacrylate, ethylene vinyl acetate, and combinations thereof. In some embodiments, the polymer is formed into a thin film. In some embodiments, the structural layer comprises a polyurethane film.

First Bonding Layer

In some embodiments, first bonding layer 240 comprises an adhesive. In some embodiments, bonding layer 240 comprises a hydrocolloid adhesive, for example Pectin, Gelatin, NaCMC—Sodium Carboxymethyl Cellulose. The adhesive may be at least 1%, at least 5%, at least 10%, at least 15%, at least 20%, at least 30%, at least 40%, or at least 50% w/w hydrocolloid. First bonding layer 240 can be composed of the same hydrocolloid adhesive as peripheral adhesive skin contact layer 230 or can be composed of a different adhesive than peripheral adhesive skin contact layer 230.

In some embodiments, first bonding layer 240 has a thickness of from about 0.1 mm to about 5 mm. In some embodiments, first bonding layer 240 has a thickness of from about 0.2 mm to about 3 mm. In some embodiments, first bonding layer 240 has a thickness of from about 0.2 mm to about 2 mm. In some embodiments, first bonding layer 240 has a thickness of from 0.2 mm to about 1 mm.

Second Bonding Layer

In some embodiments, second bonding layer 260 comprises an adhesive. In some embodiments, second bonding layer 260 comprises a hydrocolloid adhesive, for example Pectin, Gelatin, NaCMC—Sodium Carboxymethyl Cellulose. The adhesive may be at least 1%, at least 5%, at least 10%, at least 15%, at least 20%, at least 30%, at least 40%, or at least 50% w/w hydrocolloid. Second bonding layer 260 can be composed of the same hydrocolloid adhesive as peripheral adhesive skin contact layer 230 or can be composed of a different adhesive than peripheral adhesive skin contact layer 230.

In some embodiments, second bonding layer 260 has a thickness of from about 0.1 mm to about 5 mm. In some embodiments, second bonding layer 260 has a thickness of from about 0.2 mm to about 3 mm. In some embodiments, second bonding layer 260 has a thickness of from about 0.2 mm to about 2 mm. In some embodiments, second bonding layer 260 has a thickness of from 0.2 mm to about 1 mm.

Figure 7:
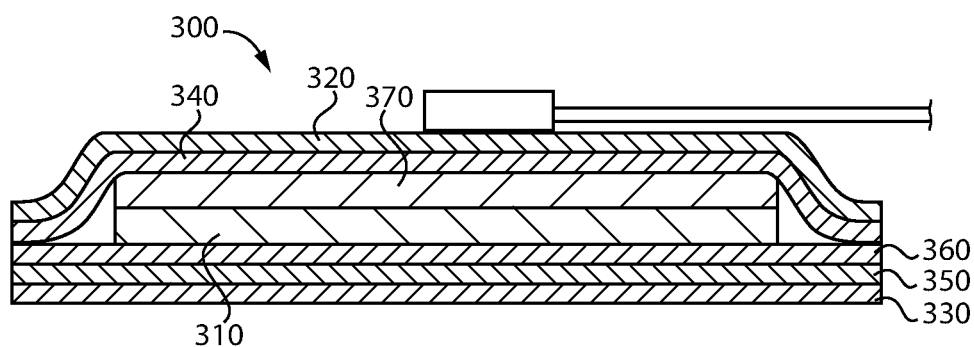
FIG. 7 illustrates a cross-sectional side view of another dressing embodiment according to the disclosure.
Figure 8:
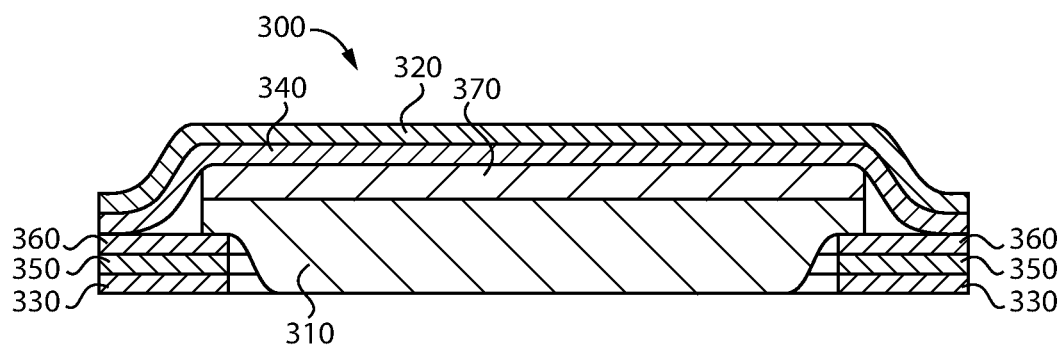
FIG. 8 illustrates another cross-sectional side view of the dressing embodiment shown in FIG. 7.

In other embodiments of the disclosure, a negative pressure distribution layer is included in the dressing. With reference to FIGS. 7 and 8, dressing 300 includes many features corresponding to those of dressings 100 and 200, and also includes negative pressure distribution layer 370 positioned between absorbent layer 310 and cover layer 320. In the embodiment shown, first bonding layer 340 is situated between negative pressure distribution layer 370 and cover layer 320. It is to be understood, however, that additional layers may be included in dressing 300 (and in other dressing embodiments described herein) between and/or among the layers shown without departing from the disclosure. For example, in one embodiment (not shown), negative pressure distribution layer 370 is positioned within absorbent layer 310 or, stated alternatively, dressing 300 includes two absorbent layers, one being positioned as shown in FIGS. 7 and 8 (absorbent layer 310) and another being positioned, fully or partly, between pressure distribution layer 370 and cover layer 320. Both absorbent layers in such an embodiment can be composed of materials as described herein in connection with absorbent layers 110, 210, 310, and can have the same composition as one another or different compositions from one another. In such an embodiment, one or more additional bonding layers (not shown) may also be included, if desired, to achieve acceptable bonding of layers to one another within the dressing.

In device 300, negative pressure distribution layer 370 has length and width dimensions corresponding to the length and width dimensions of absorbent layer 310. In other embodiments, negative pressure distribution layer 370 has dimensions different than absorbent layer 310. With the layers bonded together as shown, when peripheral skin contact layer 330 is affixed to a patient's skin surrounding a wound, negative pressure distribution layer 370, is also situated, along with absorbent layer 310, within an airtight sealed chamber of dressing 300 that is formed by peripheral skin contact layer 330, structural layer 350, second bonding layer 360 and first bonding layer 340, together with cover layer 320 and the patient's skin. Within the chamber, the patient's wound is in fluid communication with absorbent layer 310, negative pressure distribution layer 370 and aperture 228 in cover layer 320.

Negative Pressure Distribution Layer

In some embodiments, negative pressure distribution layer 370 is gas and liquid permeable and particularly moisture vapour permeable and serves to aid access of exudate to a greater area of absorbent layer 310 by distributing negative pressure laterally over dressing 300 and allowing exudate to spread under negative pressure distribution layer 370. Negative pressure distribution layer 370 also serves to even out the negative pressure applied to the wound over the whole dressing. Negative pressure distribution layer 370 preferably distributes exudate and negative pressure over the dressing. In this way, uptake of exudate by absorbent layer 310 is maximised and a more uniform transfer of negative pressure to the wound, or dressing 300, is optimized.

In some embodiments, negative pressure distribution layer 370 is a foam layer such as a polyester foam of the type XD4200AS manufactured by Caligen or another suitable reticulated foam. In other embodiments, negative pressure distribution layer 370 can comprise or be formed from any suitable material, for example, a material which can allow the transport of negative pressures to a wound site and/or which can channel and/or wick wound fluid and/or wound debris away from the wound site. For example, negative pressure distribution layer 370 can comprise or be formed from a material selected from the group consisting of a nonwoven material, a polymer and a combination thereof. In some embodiments, negative pressure distribution layer 370 may be formed from a nonwoven material. The nonwoven material may comprise natural fibers, synthetic fibers, continuous fibers, staple fibers, discontinuous fibers, bicomponent fibers and combinations thereof. In some embodiments, the nonwoven material may comprise polyolefin fibers (e.g., polypropylene, polyethylene), polyester, polyethylene terephthalate (PET), nylon, cotton, and combinations and copolymers thereof. A nonwoven material may be formed from various process known in the art, for example, meltblowing processes, spunbonding processes, spunlaid processes, airlaid processes, wetlaid processes, thermal bonded processes, bonded carded web processes, and combinations thereof. Examples of non-woven materials include, but are not limited to, co-polyester from Libeltex BVBA and HRM or polyolefin fibers in a matrix from Essentra.

In some embodiments, negative pressure distribution layer 370 may be formed from a polymer, for example, a thermoplastic elastomer (TPE), silicone, or a foam.

Examples of TPE include, but are not limited to styrene ethylene butylene styrene (SEBS) copolymers or thermoplastic polyurethane (TPU). Negative pressure distribution layer 370 may be formed by combining sheets of TPE or TPU having a thickness between about 0.2 mm and about 2.0 mm. In some embodiments, the sheets of TPE or TPU may be bonded, welded, adhered, or otherwise coupled to one another. For example, in some embodiments, the sheets of TPE or TPU may be welded using radiant heat, radio-frequency welding, or laser welding. Supracor, Inc., Hexacor, Ltd., Hexcel Corp., and Econocorp, Inc. may produce suitable TPE or TPU sheets for the formation of negative pressure distribution layer 370. In some embodiments, negative pressure distribution layer 370 may be formed from a 3D textile, also referred to as a spacer fabric. Suitable 3D textiles may be produced by Heathcoat Fabrics, Ltd., Baltex, and Mueller Textil Group.

In some embodiments, negative pressure distribution layer 370 may be formed from foam. For example, cellular foam, open-cell foam, reticulated foam, or porous tissue collections, may be used to form negative pressure distribution layer 370. In some embodiments, negative pressure distribution layer 370 may be formed of grey foam or Zotefoam. Grey foam may be polyester polyurethane foam having about 60 pores per inch (ppi). Zotefoam may be a closed-cell, cross-linked polyolefin foam. In some non-limiting examples, negative pressure distribution layer 370 may comprise or consist essentially of be reticulated polyurethane foam such as found in GRANUFOAM™ dressing or V.A.C. VERAFLO™ dressing, both available from Kinetic Concepts, Inc. of San Antonio, Tex.

In some embodiments, negative pressure distribution layer 370 may comprise or consist essentially of foam that is mechanically or chemically compressed to increase the density of the foam at ambient pressure. Foam that is mechanically or chemically compressed may be referred to as compressed foam or felted foam. Compressed foam may be characterized by a firmness factor, which may be defined as a ratio of the density of foam in a compressed state to the density of the same foam in an uncompressed state. For example, a firmness factor of 5 may refer to compressed foam having a density that is five times greater than a density of the same foam in an uncompressed state. Mechanically or chemically compressing foam may also reduce a thickness of the foam at ambient pressure when compared to the same foam that has not been compressed. Reducing a thickness of foam by mechanical or chemical compression may increase a density of the foam, which may increase the firmness factor of the foam. Increasing the firmness factor of foam may increase a stiffness of the foam in a direction that is parallel to a thickness of the foam. For example, increasing a firmness factor of negative pressure distribution layer 370 may increase a stiffness of negative pressure distribution layer 370 in a direction that is parallel to the thickness of the layer. In some embodiments, negative pressure distribution layer 370 may have a density of about 0.03 grams per centimeter$^3$ (g/cm$^3$) in its uncompressed state. In its compressed state, negative pressure distribution layer 370 may have a firmness factor (FF) of about 5, and the density may be about 0.15 g/cm$^3$.

Generally, if compressed foam is subjected to negative pressure, the compressed foam exhibits less deformation or compression set than a similar uncompressed foam. If negative pressure distribution layer 370 is formed of compressed foam, the thickness of negative pressure distribution layer 370 may deform less than if negative pressure distribution layer 370 is formed of a comparable uncompressed foam. The decrease in deformation may be caused by the increased stiffness as reflected by the firmness factor. If subjected to the stress of negative pressure, negative pressure distribution layer 370 formed of compressed foam may flatten less than negative pressure distribution layer 370 that is formed from uncompressed foam. Consequently, when negative pressure is applied to negative pressure distribution layer 370, the stiffness of negative pressure distribution layer 370 in the direction parallel to the thickness of negative pressure distribution layer 370 can allow negative pressure distribution layer 370 to be more compliant or compressible in other directions, e.g., a direction parallel to the wound surface. The pore size of a foam material may vary according to needs of negative pressure distribution layer 370 and the amount of compression of the foam. For example, in some embodiments, uncompressed foam may have pore sizes in a range of about 400 microns to about 600 microns. If the same foam is compressed, the pore sizes may be smaller than when the foam is in its uncompressed state.

In some embodiments, negative pressure distribution layer 370 may be formed from a polymer via injection molding or extrusion techniques.

In some embodiments, negative pressure distribution layer 370 may be a single layer, for example as shown in FIGS. 7 and 8. Alternatively, negative pressure distribution layer 370 may be multilayered. For example, negative pressure distribution layer 370 may comprise two or more layers, three or more layers, four or more layers, etc.

Dressing Used in Vacuum Wound Therapy

In another aspect of the present disclosure, the dressing described in previous embodiments contains a connector to be used for fluid communication through the layers. In one embodiment, a connector is coupled to the cover layer such that the connector allows fluid communication with the sealed space beneath the cover layer. The connecter is affixed to the aperture in the cover layer. The connector can be connected to a device used to produce a vacuum (such as a vacuum pump) in order to produce a reduced pressure under the cover layer.

In some embodiments, the connector can be constructed from semi-rigid material such as polyurethane film or polyvinyl chloride. Non-limiting examples of rigid or semi-rigid materials include silicone, acrylics, cyanoacrylate, rubbers, foams, cellulose, polyurethanes, polyethylenes, polyvinyl chlorides, ethylenevinyl acetates, polypropylenes, polytetrafluorethylenes, and polyisobutylenes. In some embodiments, the connector may contain additional textile material layers in order to slow down or modulate exudate draining. In some embodiments, the connector may optionally contain a change disk indicator to alert the user when it is time to change the dressing.

In other embodiments, dressings disclosed herein can be configured for connection to a vacuum pump or other negative pressure source, for example, using flexible tubes. In this way, a fluid communication pathway is provided from the wound, through one or more layers of absorbent material disposed in the dressing, to the negative pressure source. The fluid communication pathway may extend through an aperture in the cover layer to the interior lumen of a tube, optionally via the interior lumen or conduit of a flexible connector. A typical flexible connector is elongate with an interior lumen or conduit that runs parallel to the longitudinal axis of the flexible connector, wherein the flexible connector is attachable to the opening in the cover layer of the dressing in an orientation such that the longitudinal axis of the flexible connector is substantially parallel to the plane of the cover layer. The flexible member may comprise a head portion for securement to the cover layer via adhesive or other means. Typically, the fluid communication pathway extends from the interior lumen or conduit of the flexible connector through the opening in the cover layer in a direction substantially perpendicular to the longitudinal axis of the flexible connector. Once secured, a fluid-tight seal may be formed between the flexible connector and the cover layer.

In use, the dressing embodiments described herein may be secured to the skin surrounding a wound and to a conduit that is configured for connection to a source of negative pressure by a connector located at the distal end of the conduit. Negative pressure is applied to the wound by the application of negative pressure through a pathway for fluid leading from the wound, through the absorbent layer, the aperture in the cover layer and to the distal end of the conduit. Optional fenestrations that may be present in the absorbent layer, assist with the absorbance of exudate and that application of negative pressure.

Device for Vacuum Wound Therapy

In another aspect of this present disclosure, the dressing according to any embodiment disclosed herein can include a mobile vacuum pump affixed the dressing in fluid communication with the aperture defined in the cover layer of the dressing. In some embodiments, the dressing includes an "on board" vacuum system that includes a pump that is sufficiently small to be attached directly to the dressing. Such a configuration enables the manufacture and use of disposable dressing/pump combinations.

While a number of discrete embodiments have been described, aspects of each embodiment may not be specific to only that embodiment and it is specifically contemplated that features of embodiments may be combined with features of other embodiments. As will be appreciated from the descriptions herein and the associated Figures, a wide variety of aspects and embodiments are contemplated by the present disclosure, examples of which include, without limitation, the aspects and embodiments listed below:

A unitary negative pressure wound dressing construct that includes: (i) an absorbent layer having a first surface for contacting a wound and a second surface opposite the first surface, the absorbent layer comprising a gelling absorbent material, wherein the absorbent layer has a perimeter border, (ii) a cover layer having a first surface facing the absorbent layer and a second surface opposite the first surface, wherein the cover layer has a perimeter border having dimensions greater than dimensions of the absorbent layer perimeter such that the perimeter border of the cover layer extends beyond the perimeter border of the absorbent layer, and (iii) a peripheral adhesive skin contact layer attached to the first surface of the absorbent layer adjacent the perimeter border of the absorbent layer, wherein the peripheral adhesive skin contact layer defines a window through which the absorbent layer is able to contact the wound, and wherein the peripheral adhesive skin contact layer comprises a hydrocolloid adhesive, wherein the peripheral adhesive skin contact layer has a perimeter border having dimensions greater than the dimensions of the absorbent layer perimeter such that the perimeter border of the peripheral adhesive skin contact layer extends beyond the perimeter border of the absorbent layer, wherein the perimeter border of the cover layer and the perimeter border of the peripheral skin contact layer are bonded together to form a seal, wherein the peripheral adhesive skin contact layer is operable to adhere to skin surrounding a wound, and wherein the cover layer defines an aperture configured for connection to a source of negative pressure.

A dressing in accordance with any other embodiment disclosed herein, wherein the dimensions of the perimeter border of the absorbent layer are greater than dimensions of a wound to be covered by the dressing.

A dressing in accordance with any other embodiment disclosed herein, wherein the cover layer is water impermeable and air and vapour permeable.

A dressing in accordance with any other embodiment disclosed herein, wherein the peripheral adhesive skin contact layer and the cover layer are operable to form an air-tight seal between the absorbent layer and an external environment of the dressing when the dressing is applied over a wound and a source of negative pressure is sealingly connected to the aperture.

A dressing in accordance with any other embodiment disclosed herein, wherein the peripheral adhesive skin contact layer has a thickness of from about 0.1 mm to about 5 mm.

A dressing in accordance with any other embodiment disclosed herein, wherein the peripheral adhesive skin contact layer has a width of from about 2 cm to about 6 cm.

A dressing in accordance with any other embodiment disclosed herein, further comprising a first bonding layer positioned between the absorbent layer and the cover layer.

A dressing in accordance with any other embodiment disclosed herein, wherein the first bonding layer comprises a layer of hydrocolloid adhesive.

A dressing in accordance with any other embodiment disclosed herein, wherein the first bonding layer has a thickness of from about 0.2 mm to about 2 mm.

A dressing in accordance with any other embodiment disclosed herein, further comprising a structural layer corresponding to the peripheral adhesive skin contact layer and having a first surface bonded to the peripheral adhesive skin contact layer, and a second bonding layer corresponding to the peripheral adhesive skin contact layer and positioned in contact with a second surface of the structural layer that is opposite the first surface of the structural layer, wherein the structural layer is positioned between, and sealingly bonded to, the peripheral adhesive skin contact layer and the second bonding layer, and wherein the second bonding layer is sealingly bonded to a continuous portion of the first surface of the absorbent layer that is adjacent the full perimeter border of the absorbent layer.

A dressing in accordance with any other embodiment disclosed herein, wherein the peripheral adhesive skin contact layer, the second bonding layer and the cover layer are operable to form an air-tight seal between the absorbent layer and an external environment of the dressing when the dressing is applied over a wound and a source of negative pressure is sealingly connected to the aperture.

A dressing in accordance with any other embodiment disclosed herein, wherein the structural layer comprises a polyurethane film.

A dressing in accordance with any other embodiment disclosed herein, wherein the second bonding layer has a thickness of from about 0.2 mm to about 2 mm.

A dressing in accordance with any other embodiment disclosed herein, further comprising a first bonding layer positioned between the absorbent layer and the cover layer, a structural layer corresponding to the peripheral adhesive skin contact layer and having a first surface bonded to the adhesive skin contact layer, and a second bonding layer corresponding to the peripheral adhesive skin contact layer and positioned in contact with a second surface of the structural layer that is opposite the first surface of the structural layer, wherein the structural layer is positioned between, and sealingly bonded to, the peripheral adhesive skin contact layer and the second bonding layer, and wherein the second bonding layer is sealingly bonded to a continuous portion of the first surface of the absorbent layer that is adjacent the full perimeter border of the absorbent layer.

A dressing in accordance with any other embodiment disclosed herein, wherein the gelling absorbent material comprises a gel-forming fiber or filament.

A dressing in accordance with any other embodiment disclosed herein, wherein the gel-forming fiber or filament comprising chemically-modified cellulose, alginate, carboxymethyl cellulose, or combinations thereof.

A dressing in accordance with any other embodiment disclosed herein, wherein the absorbent layer comprises stitches.

A dressing in accordance with any other embodiment disclosed herein, wherein the absorbent layer further comprises an antimicrobial agent.

A dressing in accordance with any other embodiment disclosed herein, wherein the cover layer comprises a member selected from the group consisting of a polyurethane (PU), a polyvinyl chloride (PVC), a silicone elastomer, a fluoropolymer, and combinations thereof.

A dressing in accordance with any other embodiment disclosed herein, further comprising a source of negative pressure sealingly connected to the aperture and in fluid communication with the absorbent layer.

A dressing in accordance with any other embodiment disclosed herein, wherein the source of negative pressure comprises a pump connected to the aperture with a conduit.

A dressing in accordance with any other embodiment disclosed herein, further comprising a negative pressure distribution layer positioned between the absorbent layer and the cover layer.

A dressing in accordance with any other embodiment disclosed herein, wherein the negative pressure distribution layer comprises an open cell foam layer.

A dressing in accordance with any other embodiment disclosed herein, wherein the open cell foam layer is hydrophobic.

A dressing in accordance with any other embodiment disclosed herein, further comprising a connector attached to the cover layer over the aperture and configured for connection to a conduit to communicate negative pressure from the conduit to the wound through the aperture.

A dressing in accordance with any other embodiment disclosed herein, wherein the connecter comprises polyurethane or polyvinylchloride.

A dressing in accordance with any other embodiment disclosed herein, wherein the connecter comprises a change indicator.

A disposable negative pressure wound therapy device that includes: (i) a disposable pump for generating negative pressure, and (ii) a dressing in accordance with any dressing embodiment disclosed herein for covering and protecting a wound, wherein the cover layer defines an aperture connected to the pump.

A device in accordance with any other embodiment disclosed herein, further comprising: (iii) a conduit defining a lumen that provides fluid communication between the pump and the aperture defined in the cover layer of the dressing, whereby operation of the pump creates negative pressure at the site of a wound when the dressing is affixed over the wound by pressure sealing the peripheral adhesive skin contact layer to skin surrounding the wound.

While embodiments of the present disclosure have been shown and described herein, it is to be understood by those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A unitary negative pressure wound dressing construct comprising:
    an absorbent layer having a first surface for contacting a wound and a second surface opposite the first surface, the absorbent layer comprising a gelling absorbent material, wherein the absorbent layer has a perimeter border,
    a cover layer having a first surface facing the absorbent layer and a second surface opposite the first surface, wherein the cover layer has a perimeter border having dimensions greater than dimensions of the absorbent layer perimeter such that the perimeter border of the cover layer extends beyond the perimeter border of the absorbent layer,
    a peripheral adhesive skin contact layer attached to the first surface of the absorbent layer adjacent the perimeter border of the absorbent layer, wherein the peripheral adhesive skin contact layer defines a window through which the absorbent layer is able to contact the wound, and wherein the peripheral adhesive skin contact layer comprises a hydrocolloid adhesive, and
    a second bonding layer positioned in contact with the first surface of the absorbent layer,
    wherein the peripheral adhesive skin contact layer has a perimeter border having dimensions greater than the dimensions of the absorbent layer perimeter such that the perimeter border of the peripheral adhesive skin contact layer extends beyond the perimeter border of the absorbent layer,
    wherein the second bonding layer is sealingly bonded to a continuous portion of the first surface of the absorbent layer that is adjacent the full perimeter border of the absorbent layer,
    wherein the perimeter border of the cover layer and the perimeter border of the peripheral skin contact layer are bonded together to form a seal,
    wherein the peripheral adhesive skin contact layer is operable to adhere to skin surrounding a wound, and
    wherein the cover layer defines an aperture configured for connection to a source of negative pressure.

2. The dressing of claim 1, wherein the dimensions of the perimeter border of the absorbent layer are greater than dimensions of a wound to be covered by the dressing.

3. The dressing of claim 1, wherein the cover layer is water impermeable and air and vapour permeable.

4. The dressing of claim 1, wherein the peripheral adhesive skin contact layer and the cover layer are operable to form an air-tight seal between the absorbent layer and an external environment of the dressing when the dressing is applied over a wound and a source of negative pressure is sealingly connected to the aperture.

5. The dressing of claim 1, wherein the peripheral adhesive skin contact layer has a thickness of from about 0.1 mm to about 5 mm.

6. The dressing of claim 1, wherein the peripheral adhesive skin contact layer has a width of from about 2 cm to about 6 cm.

7. The dressing of claim 1, further comprising a first bonding layer positioned between the absorbent layer and the cover layer.

8. The dressing of claim 7, wherein the first bonding layer comprises a layer of hydrocolloid adhesive.

9. The dressing of claim 7, wherein the first bonding layer has a thickness of from about 0.2 mm to about 2 mm.

10. The dressing of claim 1, wherein the gelling absorbent material comprises a gel-forming fiber or filament.

11. The dressing of claim 10, wherein the gel-forming fiber or filament comprising chemically-modified cellulose, alginate, carboxymethyl cellulose, or combinations thereof.

12. The dressing of claim 10, wherein the absorbent layer comprises stitches.

13. The dressing of claim 1 wherein the absorbent layer further comprises an antimicrobial agent.

14. The dressing of claim 1, wherein the cover layer comprises a member selected from the group consisting of a polyurethane (PU), a polyvinyl chloride (PVC), a silicone elastomer, a fluoropolymer, and combinations thereof.

15. The dressing of claim 1, further comprising a source of negative pressure sealingly connected to the aperture and in fluid communication with the absorbent layer.

16. The dressing of claim 15, wherein the source of negative pressure comprises a pump connected to the aperture with a conduit.

17. The dressing of claim 1, further comprising a negative pressure distribution layer positioned between the absorbent layer and the cover layer.

18. The dressing of claim 17, wherein the negative pressure distribution layer comprises an open cell foam layer.

19. The dressing of claim 18, wherein the open cell foam layer is hydrophobic.

20. The dressing of claim 1, further comprising a connector attached to the cover layer over the aperture and configured for connection to a conduit to communicate negative pressure from the conduit to the wound through the aperture.

21. The dressing of claim 20, wherein the connecter comprises polyurethane or polyvinylchloride.

22. The dressing of claim 20, wherein the connecter comprises a change indicator.

23. A unitary negative pressure wound dressing construct comprising:
an absorbent layer having a first surface for contacting a wound and a second surface opposite the first surface, the absorbent layer comprising a gelling absorbent material, wherein the absorbent layer has a perimeter border,
a cover layer having a first surface facing the absorbent layer and a second surface opposite the first surface, wherein the cover layer has a perimeter border having dimensions greater than dimensions of the absorbent layer perimeter such that the perimeter border of the cover layer extends beyond the perimeter border of the absorbent layer,
a peripheral adhesive skin contact layer attached to the first surface of the absorbent layer adjacent the perimeter border of the absorbent layer, wherein the peripheral adhesive skin contact layer defines a window through which the absorbent layer is able to contact the wound, and wherein the peripheral adhesive skin contact layer comprises a hydrocolloid adhesive,
a structural layer corresponding to the peripheral adhesive skin contact layer and having a first surface bonded to the peripheral adhesive skin contact layer, and
a second bonding layer corresponding to the peripheral adhesive skin contact layer and positioned in contact with a second surface of the structural layer that is opposite the first surface of the structural layer,
wherein the peripheral adhesive skin contact layer has a perimeter border having dimensions greater than the dimensions of the absorbent layer perimeter such that the perimeter border of the peripheral adhesive skin contact layer extends beyond the perimeter border of the absorbent layer,
wherein the perimeter border of the cover layer and the perimeter border of the peripheral skin contact layer are bonded together to form a seal,
wherein the peripheral adhesive skin contact layer is operable to adhere to skin surrounding a wound,
wherein the cover layer defines an aperture configured for connection to a source of negative pressure,
wherein the structural layer is positioned between, and sealingly bonded to, the peripheral adhesive skin contact layer and the second bonding layer, and
wherein the second bonding layer is sealingly bonded to a continuous portion of the first surface of the absorbent layer that is adjacent the full perimeter border of the absorbent layer.

24. The dressing of claim 23, wherein the peripheral adhesive skin contact layer, the second bonding layer and the cover layer are operable to form an air-tight seal between the absorbent layer and an external environment of the dressing when the dressing is applied over a wound and a source of negative pressure is sealingly connected to the aperture.

25. The dressing of claim 23, wherein the structural layer comprises a polyurethane film.

26. The dressing of claim 23, wherein the second bonding layer has a thickness of from about 0.2 mm to about 2 mm.

27. A unitary negative pressure wound dressing construct comprising:
an absorbent layer having a first surface for contacting a wound and a second surface opposite the first surface, the absorbent layer comprising a gelling absorbent material, wherein the absorbent layer has a perimeter border,
a cover layer having a first surface facing the absorbent layer and a second surface opposite the first surface, wherein the cover layer has a perimeter border having dimensions greater than dimensions of the absorbent layer perimeter such that the perimeter border of the cover layer extends beyond the perimeter border of the absorbent layer,
a peripheral adhesive skin contact layer attached to the first surface of the absorbent layer adjacent the perimeter border of the absorbent layer, wherein the peripheral adhesive skin contact layer defines a window through which the absorbent layer is able to contact the wound, and wherein the peripheral adhesive skin contact layer comprises a hydrocolloid adhesive,
a first bonding layer positioned between the absorbent layer and the cover layer,
a structural layer corresponding to the peripheral adhesive skin contact layer and having a first surface bonded to the adhesive skin contact layer, and a second bonding layer corresponding to the peripheral adhesive skin contact layer and positioned in contact with a second surface of the structural layer that is opposite the first surface of the structural layer, wherein the peripheral adhesive skin contact layer has a perimeter border having dimensions greater than the dimensions of the absorbent layer perimeter such that the perimeter border of the peripheral adhesive skin contact layer extends beyond the perimeter border of the absorbent layer, wherein the perimeter border of the cover layer and the perimeter border of the peripheral skin contact layer are bonded together to form a seal, wherein the peripheral adhesive skin contact layer is operable to adhere to skin surrounding a wound, wherein the cover layer defines an aperture configured for connection to a source of negative pressure, wherein the structural layer is positioned between, and sealingly bonded to, the peripheral adhesive skin contact layer and the second bonding layer, and wherein the second bonding layer is sealingly bonded to a continuous portion of the first surface of the absorbent layer that is adjacent the full perimeter border of the absorbent layer.

28. A disposable negative pressure wound therapy device, comprising:

a disposable pump for generating negative pressure, and a dressing for covering and protecting a wound, the dressing comprising:

an absorbent layer having a first surface for contacting a wound and a second surface opposite the first surface, the absorbent layer comprising a gelling absorbent material, wherein the absorbent layer has a perimeter border having dimensions greater than the dimensions of a wound to be covered by the dressing, a cover layer having a first surface facing the absorbent layer and a second surface opposite the first surface, wherein the cover layer is water impermeable and air permeable, wherein the cover layer has a perimeter border having dimensions at least as great as the dimensions of the absorbent layer perimeter, and wherein a portion of the cover layer adjacent the perimeter of the cover layer is bonded to a portion of the absorbent layer adjacent the perimeter border of the absorbent layer, a peripheral adhesive skin contact layer attached to the first surface of the absorbent layer adjacent the perimeter border of the absorbent layer, wherein the peripheral adhesive skin contact layer defines a window through which the absorbent layer is able to contact the wound, and wherein the peripheral adhesive skin contact layer comprises a hydrocolloid adhesive, and a second bonding layer and positioned in contact with the first surface of the absorbent layer, wherein the cover layer defines an aperture connected to the pump, and wherein the second bonding layer is sealingly bonded to a continuous portion of the first surface of the absorbent layer that is adjacent the full perimeter border of the absorbent layer.

29. The device of claim 28, further comprising a conduit defining a lumen that provides fluid communication between the pump and the aperture defined in the cover layer of the dressing, whereby operation of the pump creates negative pressure at the site of a wound when the dressing is affixed over the wound by pressure sealing the peripheral adhesive skin contact layer to skin surrounding the wound.

\* \* \* \* \*